(12) United States Patent
Kusumoto

(10) Patent No.: US 10,967,174 B2
(45) Date of Patent: Apr. 6, 2021

(54) CARDIAC LEAD WIRE PROTECTOR

(71) Applicant: Walter Kusumoto, Chico, CA (US)

(72) Inventor: Walter Kusumoto, Chico, CA (US)

( * ) Notice: Subject to any disclaimer, the term of this patent is extended or adjusted under 35 U.S.C. 154(b) by 121 days.

(21) Appl. No.: 15/788,442

(22) Filed: Oct. 19, 2017

(65) Prior Publication Data

US 2018/0117306 A1    May 3, 2018

Related U.S. Application Data

(60) Provisional application No. 62/413,568, filed on Oct. 27, 2016.

(51) Int. Cl.
*A61N 1/05* (2006.01)
(52) U.S. Cl.
CPC ............ *A61N 1/057* (2013.01); *A61N 1/0563* (2013.01); *A61N 2001/0582* (2013.01)
(58) Field of Classification Search
CPC .................... A61N 1/057; A61N 2001/0582
See application file for complete search history.

(56) References Cited

U.S. PATENT DOCUMENTS

| 4,137,916 | A | 2/1979 | Killman |
| 5,876,429 | A | 3/1999 | Schroeppel |
| 9,161,775 | B1 * | 10/2015 | Katra ................ A61B 17/3209 |
| 2005/0228346 | A1 | 10/2005 | Goode |
| 2009/0076522 | A1 | 3/2009 | Shan |

* cited by examiner

*Primary Examiner* — Joseph M Dietrich
(74) *Attorney, Agent, or Firm* — Heisler & Associates

(57) ABSTRACT

A lead wire associated with a pacemaker, implantable cardiac defibrillator or other cardiac electric signal source is provided with a protector tube overlying at least a portion of the lead wire. In one embodiment, this protector tube is provided as a sheath tube portion of a sheath assembly along with a valve body. The valve body of the sheath assembly is fracturable and removable away from the sheath tube, leaving the sheath tube upon the lead wire as a protector tube. In other embodiments, a separate protector tube is provided and fed over the lead wire and through a sheath assembly until placed where desired. A grommet and/or plug can be provided at a proximal end of the protector tube for anchoring of the protector tube in a desired location and for plugging the protector tube, while also accommodating the lead wire passing therethrough.

18 Claims, 6 Drawing Sheets

CARDIAC LEAD WIRE PROTECTOR

CROSS-REFERENCE TO RELATED APPLICATIONS

This application claims benefit under Title 35, United States Code § 119(e) of U.S. Provisional Application No. 62/413,568 filed on Oct. 27, 2016.

FIELD OF THE INVENTION

The following invention relates to lead wires for implantable cardiac defibrillators, pacemakers and other cardiac electric signal sources. More particularly, this invention relates to protectors for cardiac electric signal source lead wires, such as tubes to overlie at least portions of the lead wire to provide additional protection against fracture of the lead wire while implanted within a patient.

BACKGROUND OF THE INVENTION

Over one million patients in the United States receive pacemakers and implantable leads for cardiac arrhythmias coupled to implantable cardiac defibrillators (ICDs). Intravascular leads extend from the pulse generator (e.g. pacemaker or ICD) to the heart and can pace, sense and shock the heart. Intravascular access by pacemaker/defibrillator leads can occur through the subclavian vein, cephalic vein, axillary vein and external jugular vein. The subclavian approach for placement of a lead is a very popular entrance point for placement of permanent intracardiac leads. The other vascular access approaches can have advantages and disadvantages. The cephalic vein can be small and not accommodate many leads, the external jugular vein approach requires tunneling above the clavicle, and the axillary approach can place the lead at an acute angle, and is more distal in the vascular tree, which can sometimes be problematic (i.e. distal entrance point in the vascular tree can decrease the maneuverability of electrodes within the heart chambers in patients with difficult anatomy or sometimes there is distal stenosis, and more proximal access is required to enter the central vascular tree). The subclavian approach despite some inherent disadvantages, remains a popular approach because of the presence of palpable anatomical landmarks without necessarily requiring fluoroscopy or ultrasound.

Fractures are a common problem with intracardiac pacemaker and implantable cardiac defibrillator leads. A common criticism of the subclavian access point is crush and fracture of the intracardiac lead between the clavicle and first rib. Fractures can occur in 1-4% of all pacemaker/ICD leads.

Sheaths are standardly used for vascular access into the subclavian vein, and are usually torn away once the cardiac lead is placed in a desired location. Pacing/implantable cardiac defibrillator lead fracture is a common problem which can potentially have catastrophic results. Lead fractures can occur anywhere along the lead depending on intrinsic qualities and design of the lead and external stresses from the body and movement of the individual. Leads placed in the subclavian vein are especially vulnerable to fracture and crush at the site of the clavicle and first rib. Despite this problem, the subclavian approach remains a popular approach among clinicians for various reasons. These reasons may include palpable anatomical landmarks without necessarily the need for fluoroscopy and ultrasound, the more central access to the vascular tree, the speed at which access can be attained, and the many years of time this approach has been accepted.

Leadless pacemaker systems and ICDs that do not require intravascular leads have also been developed. However, intravascular leads will likely be needed for dual chamber systems, patients who have defibrillators who require pacing, and for cardiac resynchronization therapy. The need for placement of intravascular leads will likely remain for the foreseeable future. Accordingly, a need exists to provide protectors for the leads, especially at critical locations, so that lead wire fracture can be eliminated or significantly reduced.

SUMMARY OF THE INVENTION

With this invention, a sheath is provided that can be partially torn away, while leaving the sheath tip and at least a portion of the sheath body as a hollow tube to remain around the lead, specifically under the clavicle for added protection against clavicular fracture. This can also give additional protection to where the lead is tied down and consequently may also be protective for leads placed at other vascular access sites, other than at the subclavian vein.

In this design, the sheath tip/body (also called the "sheath tube") is detachable from the rest of the sheath. The proximal portion of the sheath typically has a valve and side port/stopcock which is similar to current commercially available sheaths. Once the lead is placed, the valve portion of the sheath and side port are removed from the patient while the detachable tip/body remains in the patient as a protector tube and can be positioned at the clavicle for additional support and protection around this portion of the lead. The valve portion of the sheath can have a slight perforation or other zone of weakness to allow for this portion of the sheath to be torn away from the rest of the lead. There can also be a perforation or other zone of weakness between the detachable tip/body from the rest of the sheath to allow for easy separation between the detachable portion and the valve sheath portion.

Another variation to this design could be to separate the valve body of the sheath assembly from the detachable tip of the sheath by using suture scissors or a cutter to cut away the tip/body portion of the sheath that remains as a lead protector tube overlying the lead wire. The detachable tip/body of the sheath can have different tensile and surface properties from the rest of the traditional sheath. For example the detachable portion can have properties similar to a permanent pacemaker lead, but confers additional support around the lead to prevent significant crushing of the lead by external influences.

The detachable tip/body of the sheath is then typically secured using sutures and a grommet around the lead, the grommet preferably including suture attachment structures, such as wings with optional holes therein, to facilitate suturing of the grommet (and adjacent protector tube) into a fixed position with the patient. The detachable tip/body can be made of known materials with known tract record biologically and clinically, such as silicone. In addition, the silicone is likely to not affect the pacing and sensing characteristics of the lead. The sheath body tip could be detached at various locations along the sheath, depending on operator preference, vascular access utilized, or the most ideal location.

A grommet with a slit down the side can fit over the detachable tip/body to tie down the lead protector and the lead. The grommet slit would slide over the lead protector without needing to traverse the entire lead. The grommet can also have grooves to fit sutures easily to keep the sheath insulation protector in place. An inner optional plug would also preferably have a slit, with varying length, and can fit around the lead, and fits into the sheath to prevent back bleeding, and provide a consistent point(s) of contact between the protective sheath and pacemaker/ICD lead.

As an additional safety measure, a thin filament(s) could be attached to the detachable tip/body. If premature separation between the detachable tip and the sheath occurred, then the body/tip could still be easily recovered. This could be recovered over the lead, or standard J-wire and dilator. The filaments would be cut, once the sheath tip/body were at the desired location and ready to be tied down.

In one embodiment, a silicone tube is used as extra insulation and support for the lead at a stress point that is specified by the operator. This version does not have any sheath apparatus like stop cocks, and resembles a simple tube, optionally with a slit that travels the length of the tube between a proximal end and a distal end. A standard sheath assembly could be utilized, that was slightly larger than what the lead would need. Possibly 1-2 french size larger, and once the sheath is pulled out of the vasculature, this lead protector tube could be placed over the lead, which would typically have a small slit. The insulation protector tube would be advanced over the lead through the standard sheath until at the sheath tip. The standard sheath would be torn away, and the pacer/ICD lead would have additional protection at the stress point where the protector tube is placed. A known material such as silicone or polyurethane could be utilized. Such a design would likely be easier to engineer, and standard sheaths which would be familiar to the operator could be utilized.

OBJECTS OF THE INVENTION

Accordingly, a primary object of the present invention is to provide a protector tube overlying at least a portion of a lead wire associated with a pacemaker or implanted cardiac defibrillator, to protect the lead wire against fracture or other damage.

Another object of the present invention is to provide a method for protecting a lead wire from fracture or other damage, such resulting from contact with the clavicle, first rib or other body structures.

Another object of the present invention is to provide a protector tube for a lead wire which begins as a sheath assembly for lead installation, and then a portion of the sheath assembly is torn away, or otherwise separated, leaving a tip of a sheath tube portion of the sheath assembly as a protector tube upon the lead wire.

Another object of the present invention is to provide a lead protector which can confer additional protection from lead wire damage by crush between the clavicle and first rib (or other damage) at the subclavian site, and be largely if not entirely extravascular to not increase (or minimize any increase in) space requirements for the lead within the intravascular space.

Another object of the present invention is to provide additional protection for ICD and pacemaker leads with a detachable sheath tip/body remaining upon such leads after implantation to add protection from external influences at both the subclavian site and also if other access sites are utilized.

Another object of the present invention is to provide protection for the lead wire at a location of an anchoring grommet. Another common location of pacemaker/ICD lead fracture is at the grommet, where the lead is tied down to the body. The detachable sheath tip/body or other lead protector tube can add additional protection at this location.

Another object of the present invention is to provide additional protection for the lead wire to protect against fracture from repetitive or severe motion.

Another object of the present invention is to provide lead wire protection for active individuals who may be exposed to external contact and possibly repetitive/forceful motion.

Another object of the present invention is to provide a lead protector that allows for duality in function, including access assistance and then protection for intravascular leads at high stress points along the lead.

Another object of the present invention is to provide for support and protection of the lead, while allowing the use of standard sheaths but slightly larger diameter. The sheath and lead protector preferably allows for protection across different manufacturers of intravascular pacing/implantable cardiac defibrillator leads, and therefore reach a broad population.

Another object of the present invention is to reduce long-term complications associated with pacemaker and/or ICD use, such as lead fractures.

Another object of the present invention is to provide a method for reducing cardiac lead wire fracture and a cost-effective way to improve outcomes and to allow patients to be more active.

Another object of the present invention is to provide a protector for a cardiac lead wire which can be constructed from materials which are already in existence and which have favorable biocompatibility characteristics and which are easy to produce in a low-cost and reliable fashion.

Other further objects of the present invention will become apparent from a careful reading of the included drawing figures, the claims and detailed description of the invention.

DESCRIPTION OF THE PREFERRED EMBODIMENT

Figure 2:
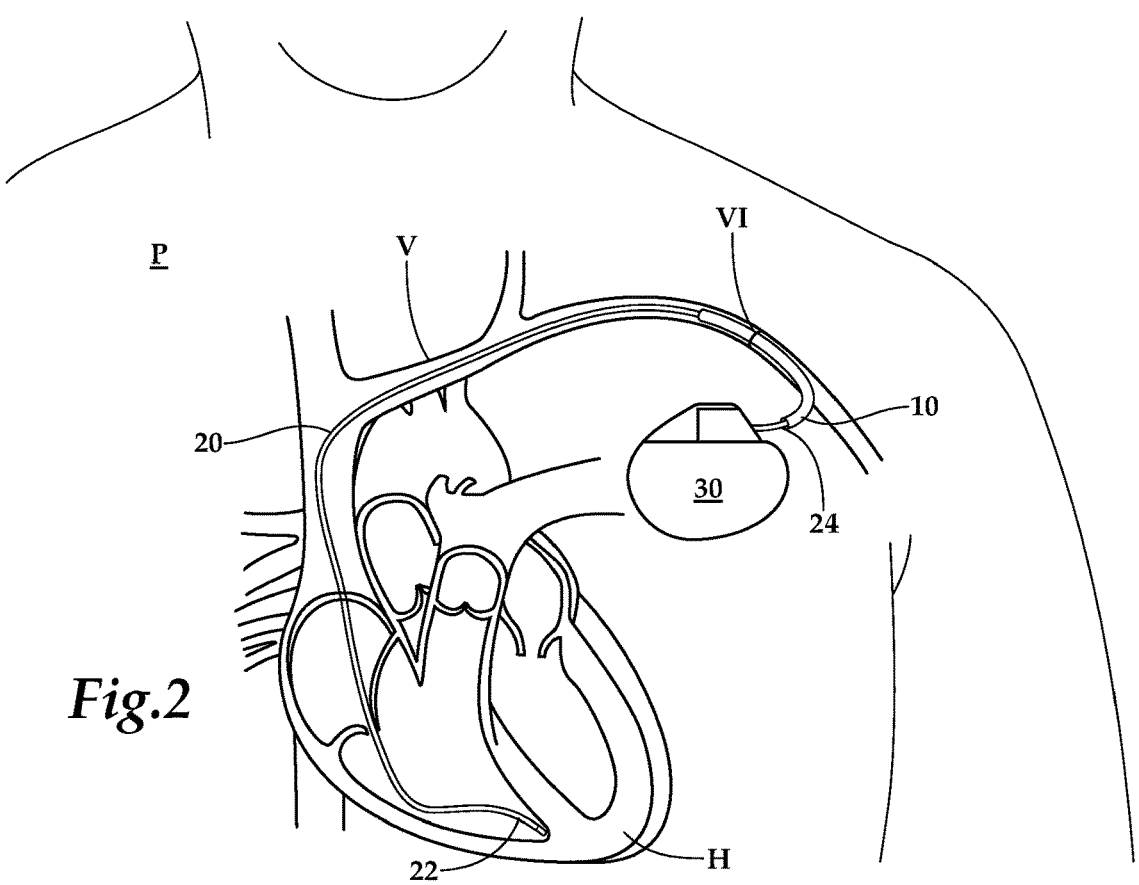
FIG. 2 is a top plan view similar to that which is shown in FIG. 1, but with a protector tube according to this invention placed over at least a portion of the lead wire, to protect the lead wire from fracture.
Figure 15:
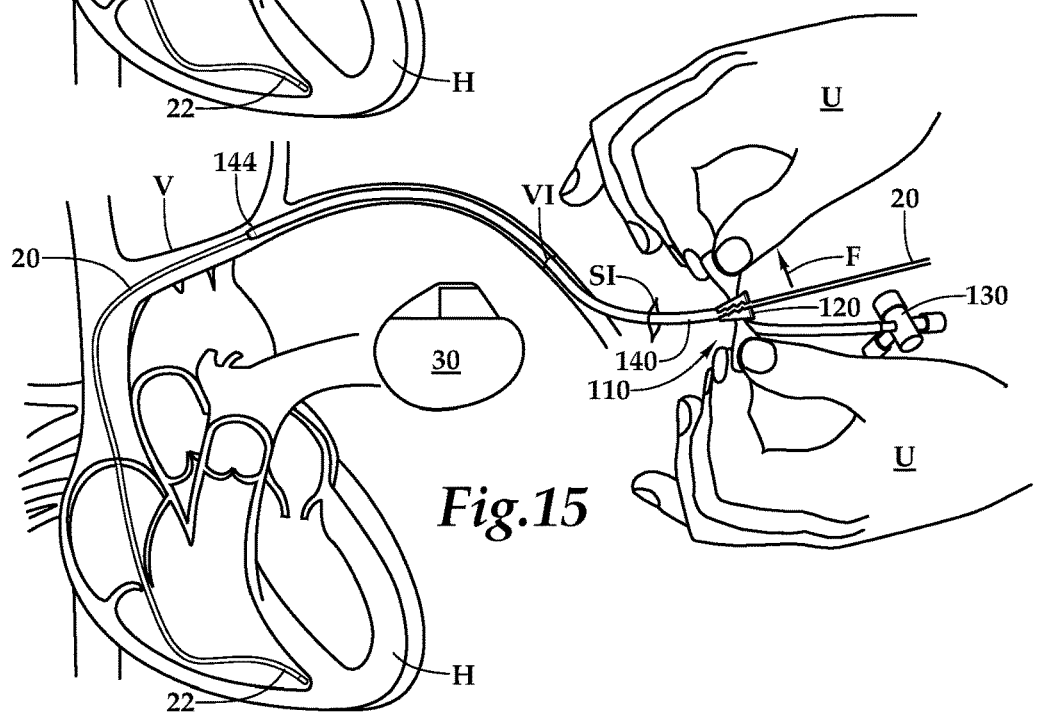
Figure 16:
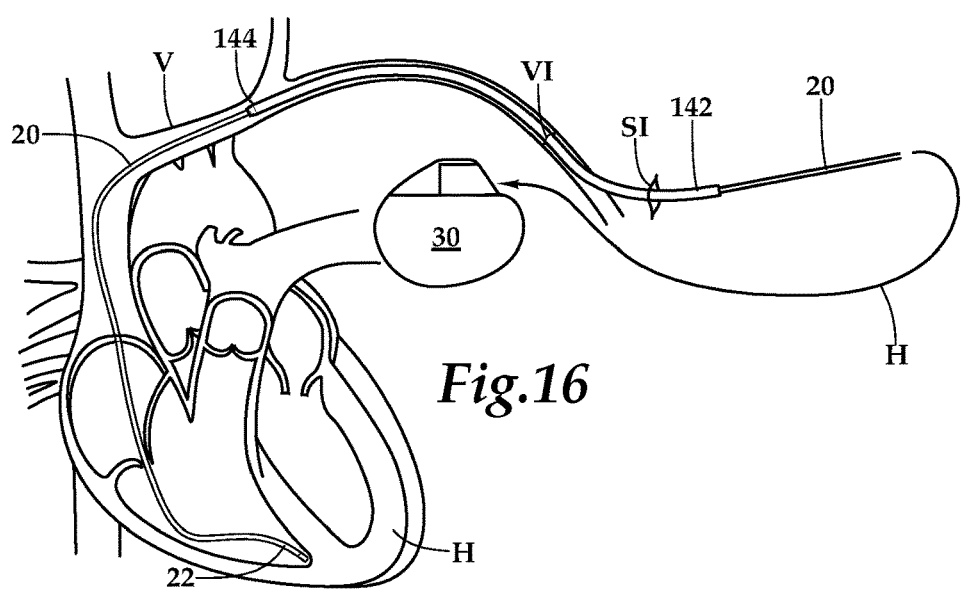
Figure 17:
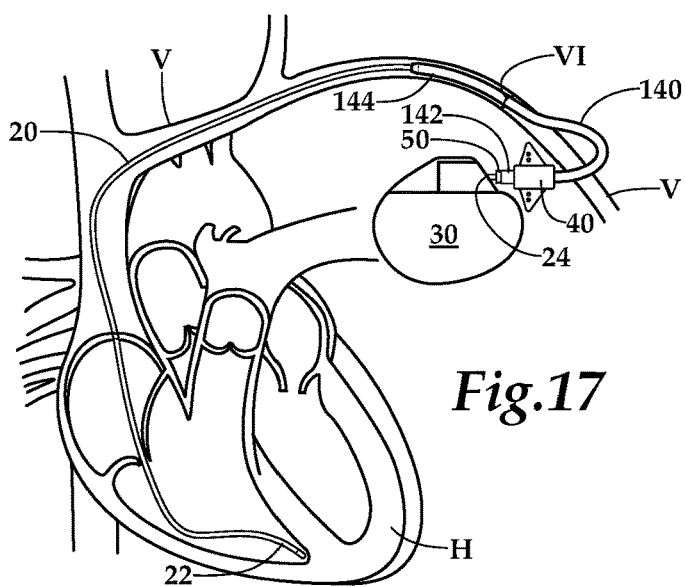
Figure 18:
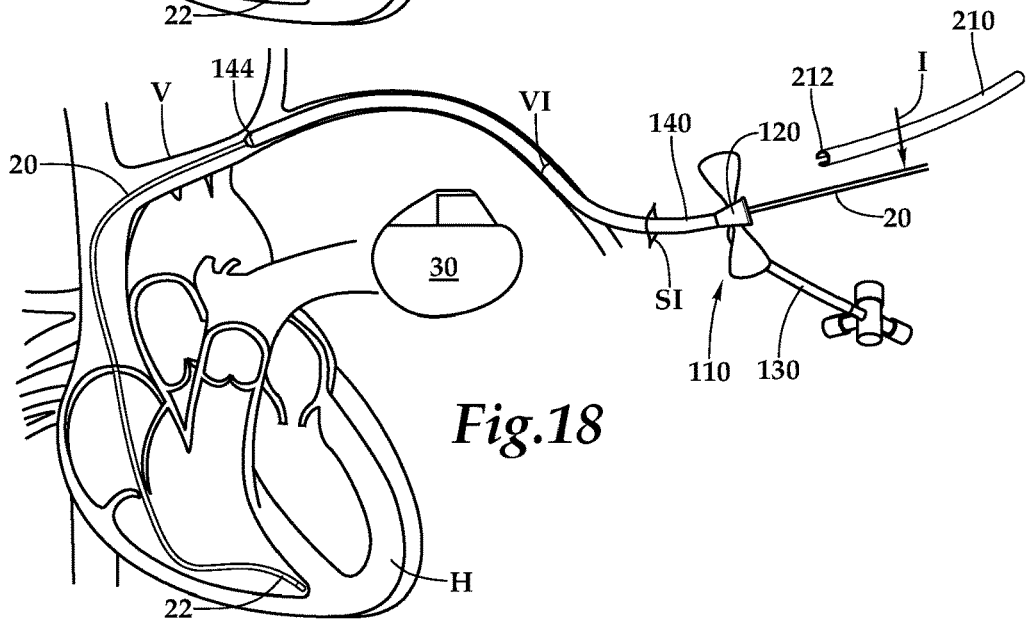
FIGS. 18 and 19 are top plan views similar to that which are shown in FIGS. 11-17, but for an alternative slitted lead protector tube which can be inserted through a slightly oversized sheath assembly for placement of the protector tube before removal of the sheath assembly, and leaving of the protector tube over a portion of the lead wire after sheath assembly removal.
Figure 19:
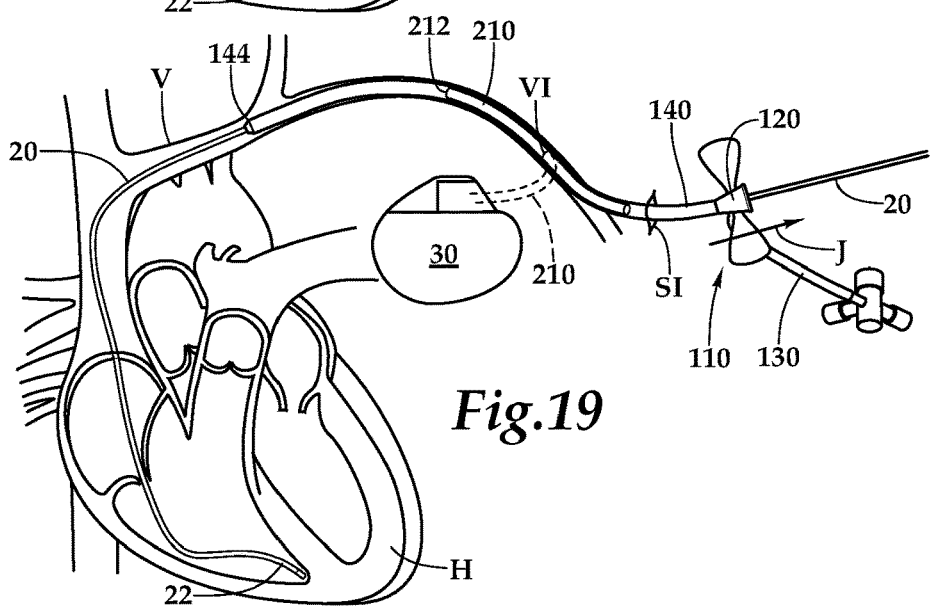

Referring to the drawings, wherein like reference numerals represent like parts throughout the various drawing figures, reference numeral 10 is directed to a protector tube (FIGS. 2, 4 and 5) which can be placed over a lead wire 20 to protect portions of the lead wire 20 between a heart H of a patient P and an electric signal source (such as a pacemaker 30 or implantable cardiac defibrillator (ICD)) typically also implanted within the patient P. The protector tube 10 can be provided as part of a sheath assembly 110 (FIGS. 6 and 7) which is initially used for lead wire 20 placement (FIGS. 11-14), and then has a portion thereof torn away, leaving a sheath 140 of the sheet assembly 110 as a protector tube for the lead wire 20 (FIGS. 15-17). In other embodiments, the protector tube 10 is provided separately and placed over the lead wire 20 for protection thereof (FIGS. 18 and 19).

Figure 5:
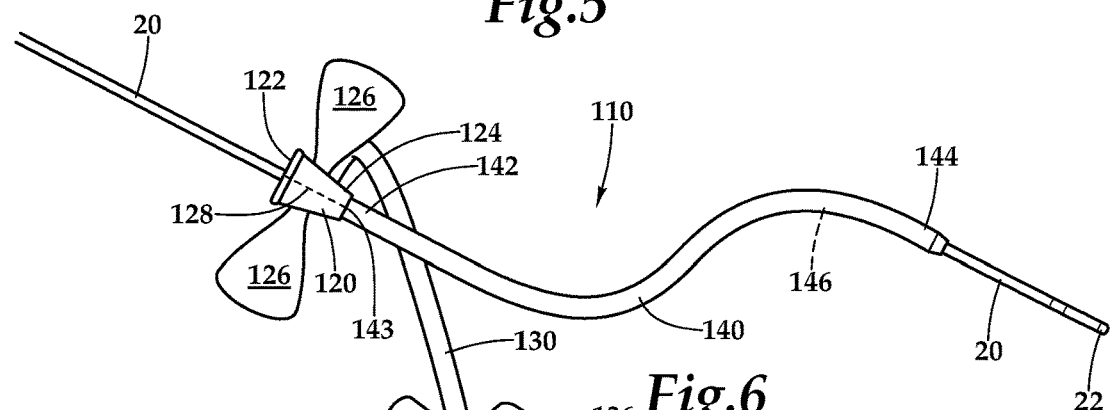
FIG. 5 is a perspective view of a combination of the lead wire and protector tube, provided together according to one embodiment of this invention to protect the lead wire and to prevent fracture thereof.
Figure 6:
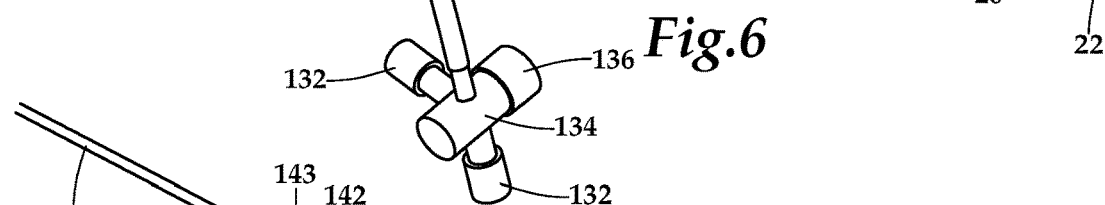
FIG. 6 is a perspective view of a lead wire installation sheath assembly shown with a lead wire passing therethrough, and utilizable in one form of this invention for initial lead wire placement, and then fracturable in a manner leaving a sheath portion of the sheath assembly in place as a protector tube over the lead wire, while a valve body and other portions of the sheath assembly are removed.
Figure 7:
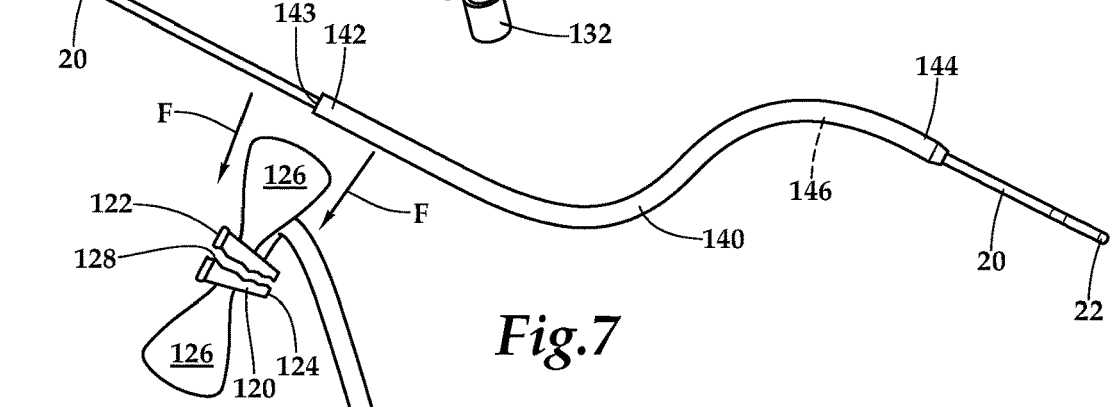
FIG. 7 is a perspective view similar to that which is shown in FIG. 6, but illustrating how portions of the sheath assembly other than the sheath tube are removed, leaving the sheath tube as a protector tube over the lead wire.

In essence, and with particular reference to FIGS. 3-7, basic details of the protector tube 10 and alternative embodiments thereof are described. The protector tube 10 in a simplest form can be any elongate tube extending from a proximal end 12 to a distal end 14, and providing a hollow core 16 between the ends 12, 14 through which the lead wire 20 can extend. In a further embodiment (FIGS. 6 and 7), the protector tube begins as a tubular sheath 140 portion of a sheath assembly 110. The assembly 110 also includes a valve body 120 and typically also a stopcock 130 subassembly extending from the valve body 120. This sheath assembly 110 is utilized for lead wire 20 placement. Thereafter, portions of the sheath assembly 110 other than the sheath 140 are separated from the sheath 140 and removed. The sheath 140 remains as the protector tube in this embodiment (FIG. 7). The lead wire 20 has a proximal interface 24 which connects to a pacemaker 30 or other electric signal source, such as an implantable cardiac defibrillator (ICD). Preferably a grommet 40 and plug 50 (FIGS. 8-10) are provided at the proximal end 12 of the protector tube 10 to allow for anchoring of the protector tube 10 and to prevent fluid flow through the protector tube 10, while also allowing the lead wire 20 to pass out of the proximal end 12 of the protector tube 10.

Figure 3:
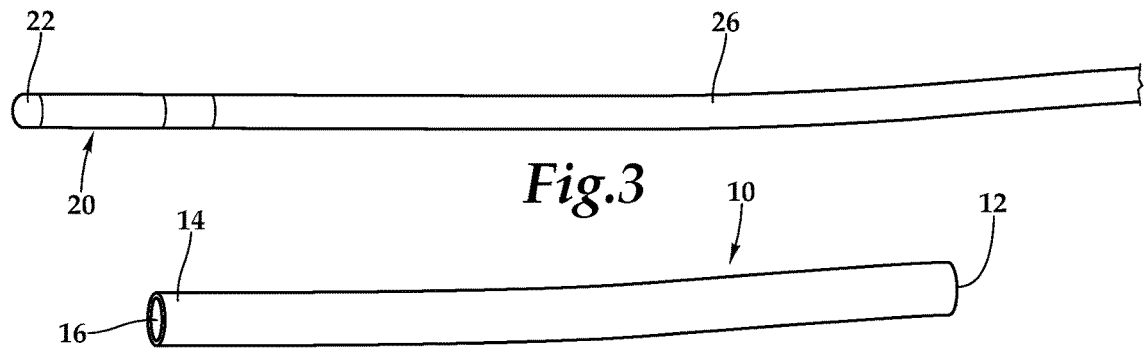
FIG. 3 is a front elevation view of a portion of a lead wire which is protected by the protector tube of this invention.
Figure 4:
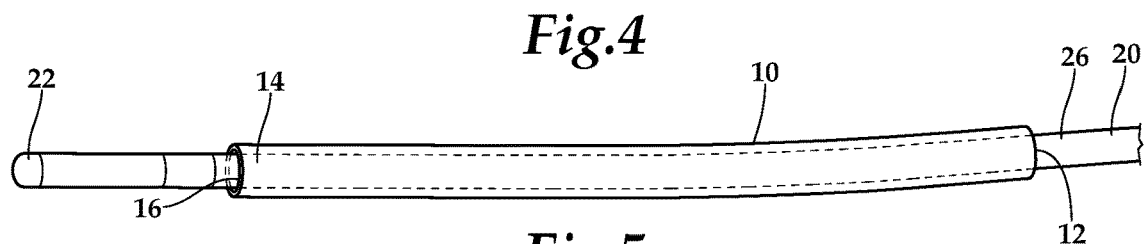
FIG. 4 is a perspective view of a protector tube according to one embodiment of this invention, with the protector tube provided as a standalone structure.

More specifically, and with particular reference to FIGS. 3-5, basic details of the protector tube 10 of this invention are described, according to an initial embodiment. The protector tube 10 is an elongate hollow cylindrical structure extending along a long axis from a proximal end 12 to a distal end 14 at opposite ends of the protector tube 10. A hollow core 16 extends between the proximal end 12 and distal end 14. Typically a cross-sectional form of the protector tube 10 is constant and generally circular in form. If desired, portions of the protector tube 10 could be thickened or otherwise strengthened at portions thereof which are perhaps most prone to lead wire 20 fracture adjacent thereto.

While the protector tube 10 is shown with a linear form, typically the protector tube 10 is formed of flexible material so that it can flex and follow a path of the lead wire as it extends along a curving path from the pacemaker 30 (or other electric signal source) to the heart H of the patient P. In one embodiment, the protector tube 10 is formed of silicone. In another embodiment, the protector tube 10 is formed of polyethylene. Other materials could alternatively be used. The ends 12, 14 are preferably not jagged or sharp, but rather rounded between an inside diameter and outside diameter of each of the ends 12, 14, so that no sharp structures are presented which could harm or irritate bodily structures of the patient P.

A length of the protector tube 10 could be provided in different lengths so that a user can select a protector tube 10 having a desired length to protect the lead wire 20 where desired. In one embodiment, a protector tube 10 has portions thereof inside of a vein V, such as the subclavian vein V, and with portions of the protector tube 10 outside of the vein V. In other embodiments, the protector tube 10 is located on portions of the lead wire 20 entirely outside of the vein V along which the lead wire 20 passes to access the heart H of the patient P. In still other embodiments, the protector tube 10 could conceivably be located entirely within the subclavian vein V or other vein V.

A diameter of the protector tube 10 is selected to be slightly larger than the lead wire 20, so that the protector tube 10 can translate along the lead wire 20 to a desired position along the lead wire 20. In other alternative embodiments, the lead wire 20 and protector tube 10 could exhibit a slight friction fit, so that movement of the protector tube 10 along the lead wire 20 is resisted somewhat, and so that once the protector tube 10 is placed where desired on the lead wire 20, it tends to remain in position upon the lead wire 20.

Various further features of the protector tube 10 could include the use of radiopaque markers adjacent one of the ends 12, 14 of the protector tube 10 (or both) and the optional inclusion of lubricant and/or medications for drug delivery from the protector tube 10, and/or to facilitate ease of passage of the lead wire 20 through the protector tube 10. A proximal end 12 other protector tube 10 can optionally include filaments attached thereto which can be readily grasped by a user or through appropriate tools handled by a user, to facilitate grasping of the protector tube 10, such as if the protector tube 10 needs to be removed for some reason or repositioned. In one embodiment, such filaments can be utilized during placement to assistant handling of the protector tube, and then cut away after placement is completed.

The lead wire 20 can be any form of electric signal conveying wire extending from an electric signal source (e.g. pacemaker 30) to the heart H or other bodily structure of the patient P which requires delivery of an electric signal thereto. This lead wire 20 typically has a distal tip 22 which is particularly configured for location within a portion of the heart H of the patient, and often including anchor structures and other structures to most effectively deliver electric current from the distal tip 22 of the lead wire 20 to adjacent cardiac tissue.

The lead wire 20 includes a proximal interface 24 opposite the distal tip 22. This proximal interface 24 is typically coupled to a pacemaker 30, or to some other electric signal source such as an implantable cardiac defibrillator (ICD). The proximal interface 24 can be connected to the pacemaker 33 through a connector which can be attached and detached, or can be permanently attached to the pacemaker 30, or can be attachable in some other fashion, such as through utilization of an appropriate crimping tool or other known electric wire connecting methodologies. If the lead wire 20 is permanently attached to the pacemaker 30, the lead wire 20 will be threaded through various structures, some of which will be broken away off of the lead wire 20 later to avoid having to disconnect the lead wire 20 from the pacemaker 30.

The lead wire 20 typically includes an outer surface 26 which includes some form of insulation jacket which resists passage of electric current therethrough. The lead wire 20 is typically in the form of an insulated wire for conducting electric current between the distal tip 22 and the proximal interface 24. This outer surface 26 not only provides for electric insulation, but also can provide some degree of protection for the lead wire 20. However, experience has shown that the lead wire 20 is still subject to fracture in certain circumstances, benefiting from the protector tube 10 being provided outboard of the lead wire 20 at least over a portion thereof for added protection. Furthermore, the lead wire 20 can be damaged in a manner which causes the insulation on the outer surface 26 of the lead wire 20 to be compromised, even though the lead wire 20 conductive pathway has not been entirely fractured. Any such damage to the lead wire 20 can be reduced by utilizing the protector tube 10 or other protector disclosed herein.

Figure 8:
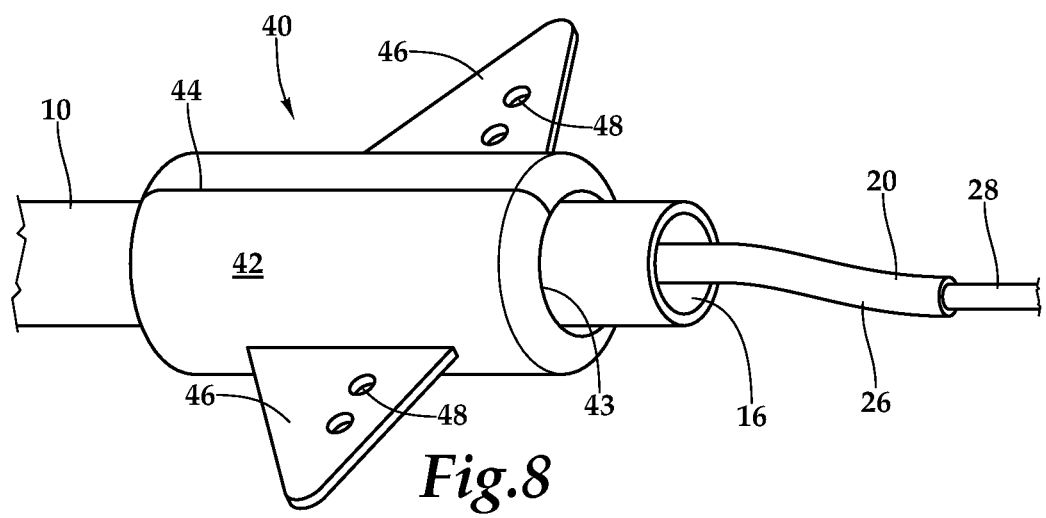
FIG. 8 is a perspective view of a detail of a proximal end of the protector tube placed over a lead wire and with a grommet over the protector tube utilizable for anchoring the protector tube and lead wire, such as with sutures, at a desired location.
Figure 9:
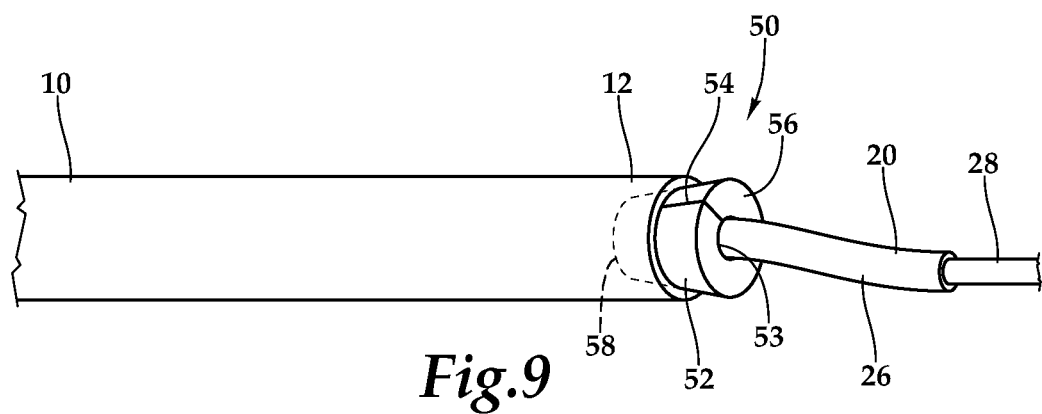
FIG. 9 is a perspective view of the protector tube of this invention placed over a lead wire, and with a plug provided at a proximal end of the protector tube, such as to prevent blood flow through the protector tube.
Figure 10:
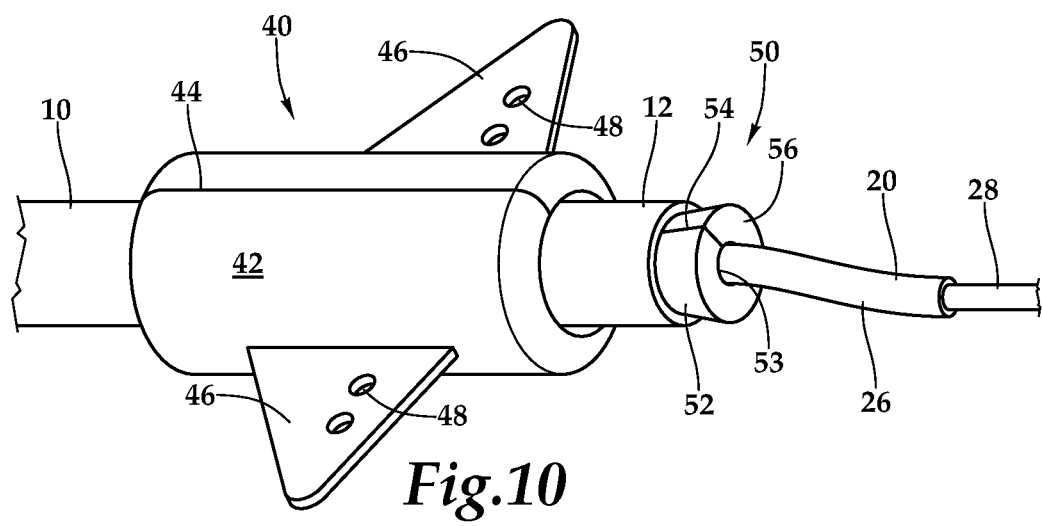
FIG. 10 is a perspective view combining the grommet of FIG. 8 with the plug of FIG. 9, shown together on a proximal end of a protector tube, and placed upon a lead wire according to one embodiment of this invention.

With particular reference to FIGS. 8-10, details of a grommet 40 and plug 50 are described, according to one embodiment of this invention. While not strictly necessary, the grommet 40 provides for physical attachment of the protector tube 10 and associated portions of the lead wire 20 to internal body structures, such as by suturing to an adjacent muscle. The grommet 40 includes a body 42 which is generally cylindrical in form with a hollow core 43 passing therethrough between ends thereof. While the grommet 40 could be fed over the protector tube 10 from an end thereof, most preferably the body 42 of the grommet 40 includes a slit 44 extending along a length thereof to allow the grommet 40 to fit over the protector tube 10 by passage of the protector tube 10 through the slit 44. The grommet 40 is preferably formed of resilient flexible material allowing the grommet 40 to be open at the slit 44 sufficiently large to snap over the proximal end 12 (or other portions) of the protector tube 10.

The grommet 40 includes at least one wing 46 and preferably a pair of wings 46 as a preferred form of suture attachment structures, to allow the grommet 40 and associated protector tube 10 and lead wire 20 to be most effectively sutured to adjacent bodily structures. The wings 46 are preferably formed of a material which can be readily penetrated by a suture needle, and optionally can include holes 48 passing through the wings 46 which provide further opportunity for suture materials to be passed through these holes 48 and conveniently anchor the grommet 40 to adjacent bodily tissues. If desired, multiple grommets 40 could be utilized on different portions of the protector tube 10.

As another alternative, a plug 50 can be provided at the distal ends 12 of the protector tube 10. This plug 50 tapers through the tapering sidewall 52 extending between a large face 56 and a small face 58. A slit 54 extends through this tapering sidewall 52 from the large face 56 to the small face 58 and accessing into a hollow bore 53 extending along an axial center line from the large face 56 to the small face 58. The plug 50 is preferably formed of resilient flexible material which is sufficiently resilient to allow the slit 54 to be opened up and fit over the lead wire 20, leaving the lead wire 20 within the bore 53 of the plug 50.

The plug 50 is sized with the large face 56 having a diameter larger than a diameter of the proximal end 12 of the protector tube 10. The small face 58 of the plug 50 is preferably sized smaller than a diameter of the proximal end 12 of the protector tube 10. This way, the plug 50 can be fitted over the lead wire 20 and then be translated until it fits into and stops up the proximal end 12 of the protector tube 10. When the protector tube 10 extends at least partially into the subclavian vein or other vein V, through a vein incision VI, potential exists for blood or other bodily fluids to pass through the protector tube 10 and out of the vein V. The plug 50 can prevent or reduce such flow from occurring.

What particular reference to FIGS. 6 and 7, details of a protector tube provided as a portion of a sheath assembly 110 are described, according to a further embodiment of this invention. The sheath assembly 110 initial includes a valve body 120 with a stopcock 130 sub-assembly extending therefrom and with a sheath tube 140 extending from the valve body 120. The valve body 120 includes an entry 122 on a first side thereof and with an interface 124 on the side of the valve body 120 opposite the entry 122. Interface 124 is coupled to the sheath tube 140 extending in an elongate fashion away from the valve body 120.

The valve body 120 allows for elongate structures such as dilators 150 and lead wires 20 to pass through the valve body 120 and through the sheath tube 140 to a location where the sheath tube 140 has been placed, such as intraluminally. Preferably, tabs 126 extend laterally from the valve body 120. A fracture line 128 or other zone of weakness preferably extends along the valve body 120 from the entry 122 to the interface 124. This fracture line 128 could be in the form of perforations or other elongate portions which is sufficiently weak that a user, such as by applying forces to the tabs 126, can cause the valve body 120 to fracture along the fracture line 128 or other zones of weakness and break off of a lead wire 20 which has been routed through the valve body 120 and into the sheath tube 140.

Importantly, the sheath tube 140 has a proximal end 142 adjacent to the valve body 120 which includes perforations 143 (FIG. 7) or some other zone of weakness which causes the sheath tube 140 to be readily separated from the valve body 120 when forces are applied there between, tending to separate them from each other. The sheath tube 140 also extends to distal end 144 opposite the proximal end 142 and with a hollow core 146 extending between the proximal end 142 and the distal end 144. It can be seen that once the sheath assembly 110 has been deconstructed by fracture and removal of the valve body 120 (and any associated stopcock 130) that this will leave the sheath tube 140 in position upon the lead wire 20 (FIG. 7). The sheath tube 140 acts as a protector tube similar to the protector tube 10 (FIGS. 3-5) that can then be positioned where desired upon the lead wire 20 for protection of the lead wire 20 and prevention of fracture or other lead wire 20 damage. Thus, the protector tube can initially be provided as the sheath tube 140 as part of the sheath assembly 110, and then have all portions of the sheath assembly 110 fractured and removed from the sheath tube 140, leaving the sheath tube 140 as the protector tube upon the lead wire 20.

Typically, the valve body 120 includes the stopcock sub-assembly 130 thereon which include ports 132 as part of a hub 134 and with a control 136 on the hub 134 for opening and closing of the ports 132. The stopcock sub-assembly 130 can allow for introduction of fluids into the valve body and on through the sheath tube 140 for delivery from the distal end 144, or can be utilized for removal of fluids, such as by placement of a syringe and applying suction to suction fluids through the sheath and out of the sheath assembly 110 through the stopcock sub-assembly 130. As one example, to verify that the distal end 144 of the sheath tube 140 has been placed within the subclavian vein V or other vein successfully, one can draw a vacuum through a syringe or other device coupled to one of the ports 132 associated with the stopcock sub-assembly 130, and draw fluid, and see what fluid is translated through the sheath tube 140, and to some extent the degree of ease with which fluid is translated through the sheath tube 140, to verify that the distal end 144 of the sheath tube 140 is in fact located where desired, such as within the vein V downstream of a vein incision VI.

Initial navigation of the distal end 144 of the sheath tube 140 is facilitated, even though the sheath tube 140 is quite flexible and would otherwise be difficult to maneuver, by placing a dilator 150 through the valve body 120 and on through the sheath tube 140, typically until the dilator 150 has a tip 154 extending out of the distal end 144 of the sheath tube 140. A handle 152 on a portion of the dilator 150 proximal to the valve body 120 is coupled to the tip 154 through the sheath tube 140 and a user can work with this handle 152 to move the tip 154 of the dilator further beyond the distal end 144 of the sheet tube 140. Other tools of a user can also be passed through the sheath assembly 110, such as for formation or adjacent of the vein incision VI and to assist in routing of the distal end 144 of the sheath tube 140 where desired. Such dilator 150 is then removed so that the lead wire 20 can be passed through the valve body 120 and sheath tube 140 of the sheath assembly 110 and for placement of the lead wire 20 where desired within the heart H of the patient P.

Figure 11:
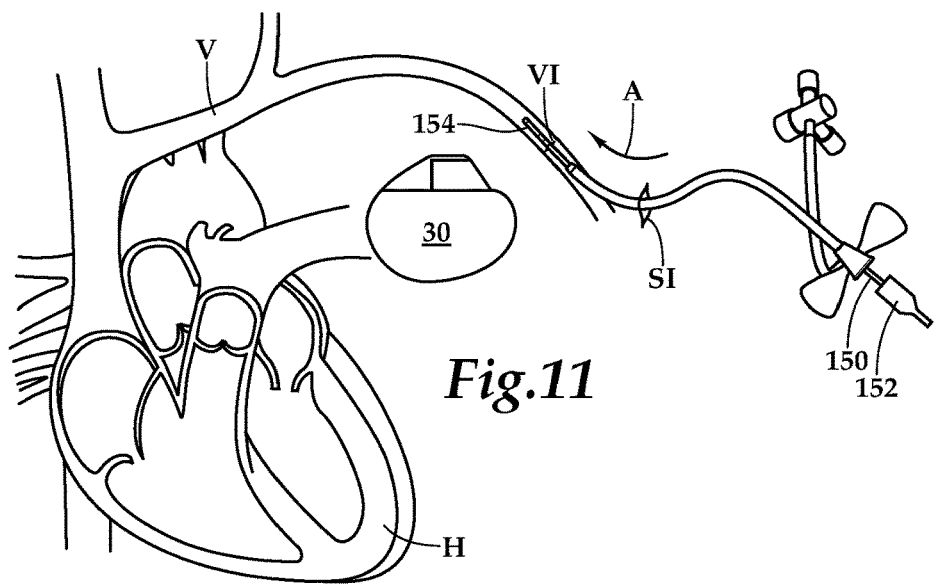
FIGS. 11-17 are top plan views of a heart of a patient along with a subclavian vein, and depicting a series of steps associated with placing a sheath of the sheath assembly into a vein leading to the heart of the patient, routing a lead wire through the sheath into the heart of the patient, fracturing the sheath assembly to leave the sheath tube as a protector tube over portions of the lead wire, and completing the system by optionally including a grommet and plug as depicted in FIGS. 8-10.
Figure 12:
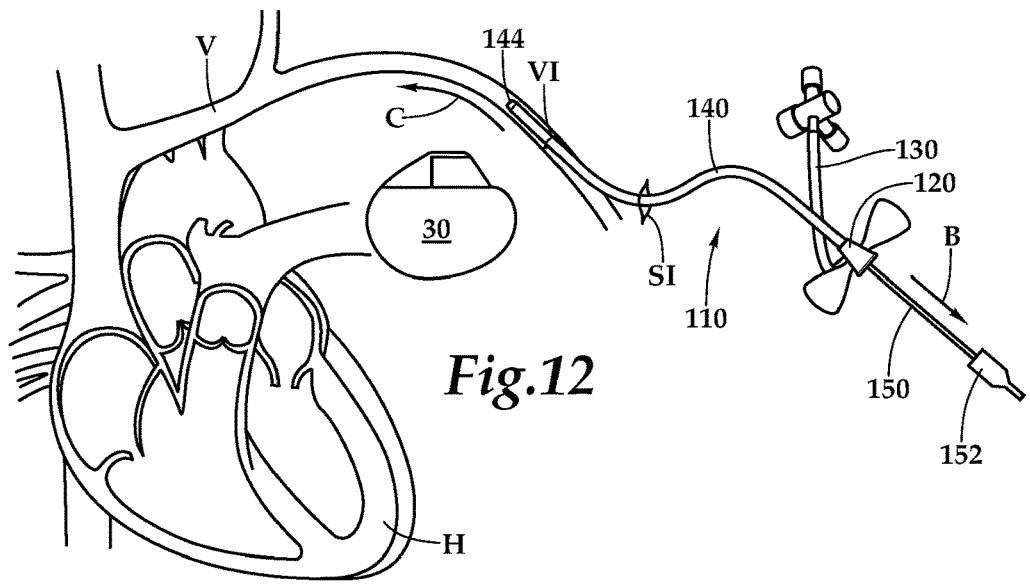
Figure 13:
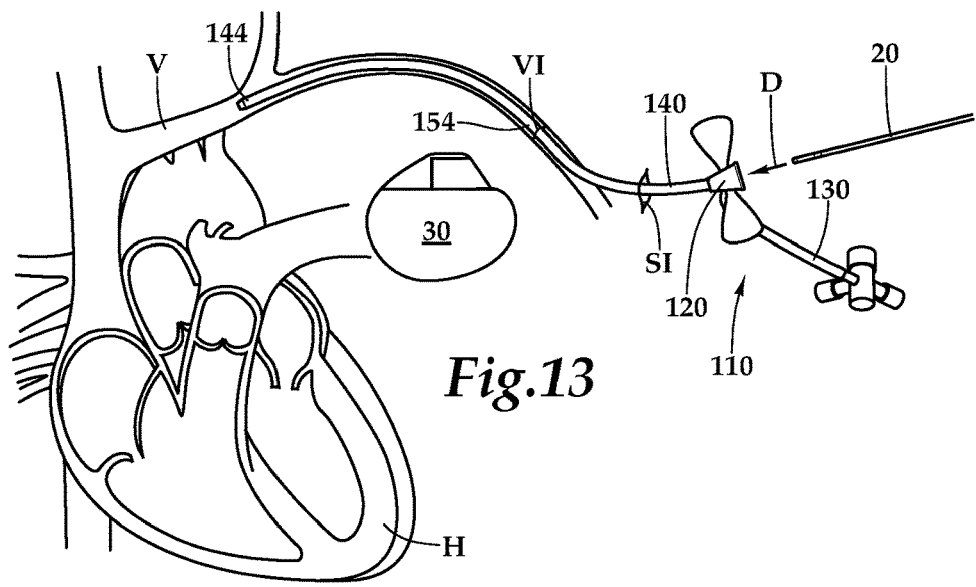
Figure 14:
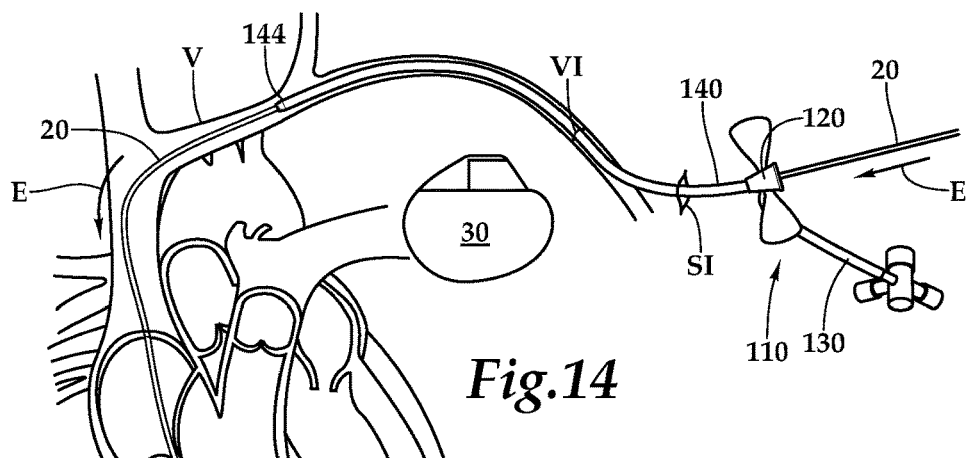

Many pacemakers 30 and other electric signal sources utilize multiple lead wires leading to different portions of the heart H or other bodily structures of the patient P. In systems where multiple lead wires are utilized, one option for fracture prevention according to this invention include routing of two or more lead wires 20 through a common protector tube 10, either according to the embodiment of FIGS. 3-5, or according to the embodiment of FIGS. 6 and 7. As a second option, each lead wire of such a multi-lead wire system can have its own separate protector tube 10 thereon, according to the embodiment of FIGS. 3-5 (or the embodiment of FIGS. 6 and 7) provided thereon for protection of each of the lead wires associated with such a multi-wire system In use and operation, and referring to FIGS. 11-17, installation of the protector tube as a sheath portion of a sheath assembly 110 is described, according to one protocol. First, subclavian access is obtained using standard techniques. The standard tear away sheath is replaced with the detachable sheath assembly 110 (FIGS. 6 and 7). The placement of the sheath assembly 110 with the sheath tube 140 within the subclavian vein V or other vein V is depicted in FIGS. 11 and 12 (along arrow A of FIG. 11 and arrow C of FIG. 12), utilizing the dilator 150 to assist in navigation and placement of the distal end 144 of the sheath tube 140 of the sheath assembly 110 where desired. The dilator 150 is then removed (along arrow B of FIG. 12). The lead wire 20 can then be routed through the sheath assembly 110 (along arrows D and E of FIGS. 13 and 14).

Figure 1:
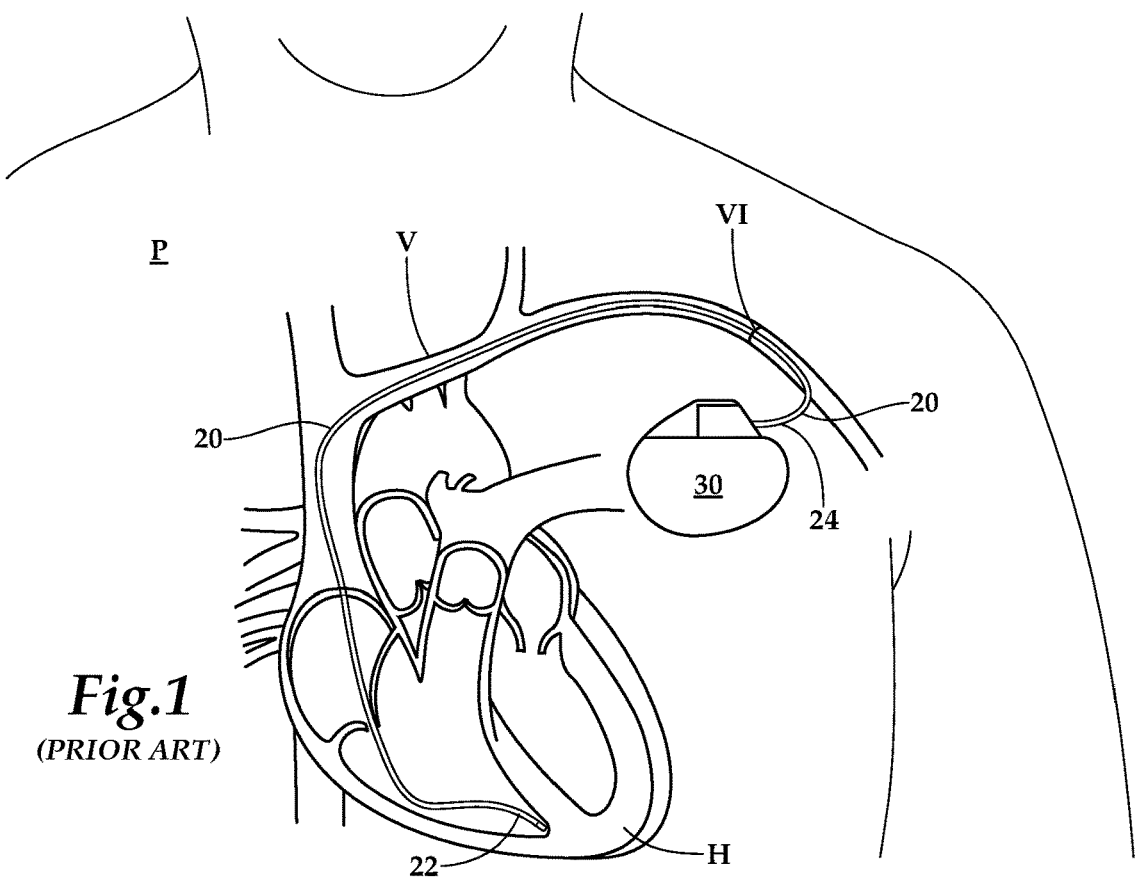
FIG. 1 is a top plan view of a heart of a patient along with a subclavian vein and electric signal source, such as a pacemaker, with a lead wire extending from the pacemaker into the heart of the patient, according to a typical prior art arrangement.

After the lead wire 20 is in position where desired (FIG. 15), the sheath assembly 110 is deconstructed, with removal of the valve body 120 and any stopcock sub-assembly 130. In particular, the valve body 120 fractured along the fracture line 128 or other zone of weakness and the perforations 143 at the proximal end 142 of the sheath tube 140, or other zone of weakness on the proximal end 142 of the sheath 140 is used to break away the valve body 120 and stopcock sub-assembly 130 from the sheath tube 140 (following arrow F of FIG. 15). The sheath tube 140 is then left as a form of protector tube (FIG. 16). The proximal interface 24 (FIGS. 1 and 2) of the lead wire 20 can be attached to the pacemaker 30 or other electric signal source (along arrow H of FIG. 16) if it was previously detached (after resizing of a length of the lead wire 20 if needed). If the lead wire 20 was already attached to the pacemaker 30, this attachment step is not required. The grommet 40 and plug 50 are optionally fitted onto the proximal end 12 of the tube 140 (FIG. 17) and appropriate sutures can be utilized for final anchoring of the protector tube in the form of the sheath tube 140.

Once the pacing lead 20 is at a desired location, the sheath/insulation protector 10, 140 location can be confirmed by fluoroscopy, and contrast can be used to confirm when the sheath is outside of the vascular tree. In addition, the sheath body can be pulled back over the pacemaker/ICD lead 20 until there is no longer any pullback of blood from the side stopcock sub-assembly 130 port 132, before removal of the valve body 120 and stopcock 130 of the sheet assembly 110 from the sheath tube 140.

Referring to FIGS. 18 and 19, if the embodiment of FIGS. 3-5 is utilized, then the lead insulation protector 10 is placed over the lead and advanced into the standard (but typically slightly oversized) sheath, until a good position is obtained. The sheath is pulled back to an extravascular location, confirmed by having no pullback of blood using a syringe from the side port of the stopcock sub-assembly 130. The sheath and insulation protector 10 can allow for additional protection for the lead 20 from the clavicle.

The protector tube 10 could be replaced with a slitted protector tube 210 (FIGS. 18 and 19) to allow the tube 210 to be opened along this slit 212 so that it can be placed upon the lead wire 20, and then be fed through the valve body 120 of a sheath assembly 110, and advanced through the sheath tube 140 to a desired location for such a slitted protector tube 210. In such an embodiment, the sheath assembly 110 would be oversized slightly to accommodate placement of the slitted protector tube 210 upon the lead wire 20 and inside of the sheath tube 140 of the sheath assembly 110. After placement of the slitted protector tube 210 where desired, the sheath assembly 110 can be backed off proximally or fractured and removed. The protector tube 10 can optionally be fitted with a grommet 40 and/or plug 50 as with previous embodiments (FIG. 17). As one option, the sheath/insulation protector 10, 140, 210 is tied down onto the pectoralis muscle. An outer grommet can be placed around where the suture is tied down.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A cardiac lead wire with protector tube system, comprising in combination:
   a lead wire having an electrically conductive pathway extending between a distal tip and a proximal interface;
   a protector tube extending from a proximal end thereof to a distal end thereof, said proximal end opposite said distal end;
   said protector tube located overlying a portion of said lead wire between said distal tip of said lead wire and said proximal interface of said lead wire;
   wherein said protector tube forms part of an original sheath assembly with a sheath tube and a removable valve body through which said lead wire can be introduced and advanced through said sheath tube, said valve body removable to leave said sheath portion of said sheath assembly as said protector tube; and
   wherein said sheath assembly includes a zone of weakness between said valve body and said sheath tube, whereby said sheath tube is manually separable from said valve body.

2. The system of claim 1 wherein said protector tube has a length which is less than a length of said lead wire.

3. The system of claim 1 wherein said proximal interface is coupled to an electric signal source including a pacemaker.

4. The system of claim 1 wherein said proximal interface is coupled to an electric signal source including an ICD.

5. The system of claim 1 wherein said protector tube is slidable along an exterior of said lead wire.

6. The system of claim 1 wherein said sheath assembly includes a zone of weakness along a length of said valve body.

7. The system of claim 1 wherein said protector tube includes a slit extending along a length of said protector tube.

8. The system of claim 1 wherein a grommet is removably coupled to said protector tube, said grommet including suture attachment structures thereon.

9. The system of claim 1 wherein a plug with a tapering sidewall and a hollow bore is located within and plugging a proximal end of said protector tube, with said lead wire passing through said hollow bore, said plug having a large face opposite a small face and with said tapering sidewall therebetween, said large face having a diameter greater than a diameter of said protector tube and said small face having a diameter smaller than a diameter of said protector tube.

10. The system of claim 1 wherein said zone of weakness extends circumferentially around an elongate central axis of said sheath tube.

11. The system of claim 10 wherein said zone of weakness includes perforations for weakening of a single mass including said sheath tube and said valve body.

12. The system of claim 11 wherein said perforations are located at an interface of said valve body defining a most distal portion of said valve body.

13. A protector tube for overlying and protecting a portion of a cardiac lead wire, the protector tube comprising in combination:
   an elongate tube extending between a proximal end and a distal end;
   a hollow core extending from said proximal end to said distal end;
   said hollow core sized to receive a cardiac lead wire passing therethrough;
   wherein said protector tube forms part of an original sheath assembly with a sheath tube and a removable valve body through which a lead wire can be introduced and advanced through said sheath tube, said valve body removable to leave said sheath portion of said sheath assembly as said protector tube; and
   wherein said sheath assembly includes a zone of weakness between said valve body and said sheath tube, whereby said sheath tube is manually separable from said valve body.

14. The protector tube of claim 13 wherein said protector tube includes a slit extending along a length of said protector tube.

15. The protector tube of claim 13 wherein said sheath assembly includes a zone of weakness along a length of said valve body.

16. The protector tube of claim 13 wherein said zone of weakness extends circumferentially around an elongate central axis of said sheath tube.

17. The protector tube of claim 16 wherein said zone of weakness includes perforations for weakening of a single mass including said sheath tube and said valve body.

18. The protector tube of claim 17 wherein said perforations are located at an interface of said valve body defining a most distal portion of said valve body.

* * * * *